United States Patent [19]

Brandhorst et al.

[11] Patent Number: 5,722,830
[45] Date of Patent: Mar. 3, 1998

[54] CONTAINER FOR STORING AND DISPENSING A DENTAL SUBSTANCE

[75] Inventors: Gerd Brandhorst, Landsberg; Wolf-Dietrich Herold, Seefeld, both of Germany

[73] Assignee: Thera Patent GmbH & Co. KG, Seefeld, Germany

[21] Appl. No.: 603,334

[22] Filed: Feb. 20, 1996

[30] Foreign Application Priority Data

Feb. 20, 1995 [DE] Germany ............... 295 02 783 U

[51] Int. Cl.⁶ ......................................... A61C 5/04
[52] U.S. Cl. ................................. 433/90; 433/89
[58] Field of Search ............................... 433/90, 89

[56] References Cited

U.S. PATENT DOCUMENTS

| | | | |
|---|---|---|---|
| 3,854,209 | 12/1974 | Franklin et al. | 433/90 |
| 4,295,828 | 10/1981 | Rudler | 433/90 |
| 4,391,590 | 7/1983 | Dougherty | 433/90 |
| 4,768,954 | 9/1988 | Dragan | 433/90 |
| 4,969,816 | 11/1990 | Drumm | 433/90 |
| 4,993,948 | 2/1991 | Cameron et al. | 433/90 |
| 5,004,124 | 4/1991 | Stefaniak et al. | 433/90 |
| 5,122,057 | 6/1992 | Discko, Jr. | 433/90 |
| 5,249,716 | 10/1993 | O'Sullivan | 282/568 |
| 5,445,523 | 8/1995 | Fischer et al. | 433/90 |

FOREIGN PATENT DOCUMENTS

| | | |
|---|---|---|
| 2 004 465 | 8/1971 | Germany . |
| 27 41 184 | 3/1979 | Germany . |
| 3420765 A1 | 5/1985 | Germany . |
| 3421823 A1 | 5/1985 | Germany . |
| 38 39 979 | 8/1990 | Germany . |
| PCT/US94/ 09982 | 3/1995 | WIPO . |

*Primary Examiner*—John J. Wilson
*Attorney, Agent, or Firm*—Foley & Lardner

[57] ABSTRACT

A container for storing and dispensing a substance, particularly a dental substance, comprises a cylindrical cartridge 20 and a dispensing nozzle 21 communicating therewith. The dispensing nozzle 21 is formed as a rigid curved tube having an inlet opening of the same diameter as the cartridge 20 and being aligned with the cartridge axis 14, whereas the dispensing opening of the nozzle 21 extends at an angle with respect to the cartridge axis 14. The nozzle 21 is circularly curved and tapers in such a way that its inner cross-sectional shape is circular throughout the length of the nozzle. The interior cross-section and the wall thickness of the nozzle 21 decrease toward the dispensing end.

17 Claims, 1 Drawing Sheet

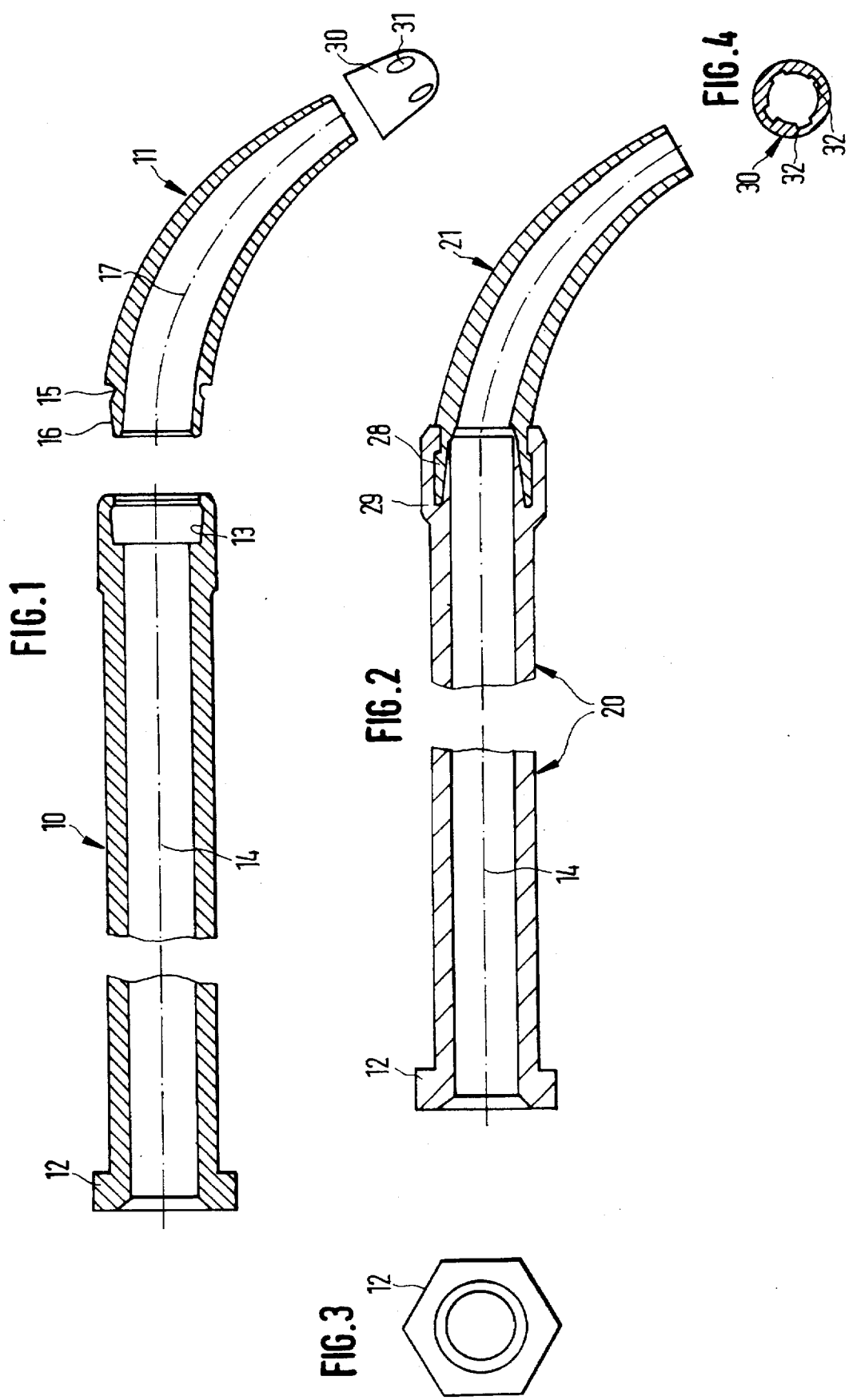

CONTAINER FOR STORING AND DISPENSING A DENTAL SUBSTANCE

BACKGROUND OF THE INVENTION

This invention relates to a container for storing and dispensing substances, particularly dental substances.

U.S. Pat. No. 4,295,828 discloses a container consisting of a rigid circular-cylindrical cartridge the front portion of which forms a curved, forwardly tapering dispensing nozzle termination in an outlet opening which is inclined with respect to the axis of the cartridge. For emptying the container, a rear flange of the cartridge is inserted into an applicator, and the substance is expelled by a piston inserted into the rear end of the cartridge.

Dental substances which are distributed in containers of this type are often sensitive to shearing forces and/or local pressure differences. In dispensing, the substance is exposed to transverse forces at those locations where the cross-sectional shape of the cartridge or dispensing nozzle changes. Transverse forces may cause decomposition of the substance and thereby undesired changed in its properties. Due to the considerable pressures which are necessary to expel pasty substances, even comparatively small changes in the cross-sectional shape may be determined.

For accurately applying the substance to confined areas, such as tooth cavities, it is desired to have a thin dispensing nozzle and to make the angle between the axis of the nozzle and the longitudinal axis at the inlet end of the cartridge not too small.

The container known from the above U.S. Pat. No. 4,295,828 is not optimal in either one of these respects. The cross-sectional shape changes at the location where the cartridge passes over into the nozzle, and the dispensing angle is small. A larger angle would result in an even more pronounced change in cross-sectional, as may be seen, e.g., in the cartridge known from German Offenlegungsschrift 3,839,979.

German Auslegeschrift 2,741,184 discloses a container having a constant cross-sectional throughout. In addition to the fact that the comparatively large dispensing opening is disadvantageous in practical use, the known construction includes a flexible tube and external stiffening member and is therefore expensive in manufacture.

The same problem exists with the container known from U.S. Pat. No. 5,249,716, in which the substance is contained in a flexible hose which is protected by a surrounding rigid, curved guide tube only during extending and only over part of its length. Otherwise, any lateral pressure exerted on the hose will be passed on to the substance.

SUMMARY OF THE INVENTION

It is an object of the present invention to devise a container, particularly for dental substances, by which especially substances that are sensitive to shearing forces and/or local pressure differentials may be stored and dispensed more safely.

This object is accomplished in accordance with the present invention by a container which includes a circular-cylindrical cartridge for receiving the substance and a dispensing nozzle communicating with the cartridge and having the shape of a rigid, curved and forwardly tapering tube, the inlet opening of the nozzle being aligned with the axis of the cartridge, and the outlet opening being inclined with respect to this axis, wherein the tube forming the dispensing nozzle has the same size at its inlet end as the cartridge, the tube being circularly curved and tapered in such a way that its inner cross-sectional shape is circular throughout the length of the nozzle down to its outlet opening.

When dispensing the mass from the container according to the invention, no sudden changes in the cross-section of the container or in the moving direction of the substance occur, so that the substance is not exposed to any local transverse or shearing forces. At the same time, the invention achieves a small outlet opening at a dispensing angle that is convenient in the practical use of the container. The circular curvature of the nozzle is of importance for permitting easy removal of the nozzle from the mould.

In a preferred embodiment, the dispensing nozzle is rotatable about the axis of the cartridge in the plane of its inlet opening. This feature is useful not only for manufacturing the nozzle but also for its handling. It permits the orientation of the nozzle to be adjusted as desired immediately prior to the dispensing step, after the container has been placed in the respective applicator. An uncomplicated way of assembling the container is achieved if the dispensing nozzle is retained in the outlet end of the cartridge by a snap-connection.

According to another embodiment of the invention, the cartridge is moulded to the dispensing nozzle. Preferably, the dispensing nozzle is provided with a rear flange which is embedded in the material of the cartridge. This embodiment is advantageous because it simplifies the manufacture of the container. With this embodiment, it may be preferable to provide a rear flange on the cartridge for engagement by an applicator, which flange has a shape different from a circular cylinder to prevent rotation of the container relative to the applicator.

In accordance with another embodiment, the wall of the dispensing nozzle has a thickness which decreases from the inlet toward the outlet opening of the nozzle. This permits the accurate dispensing of small amounts of the substance even if the cartridge has a comparatively large inner cross-section and a correspondingly small length.

In a specific embodiment of the invention, the axis at the inlet end of the dispensing nozzle is inclined with respect to the axis of the cartridge at an angle of at least 45° to 90°, preferably at least 60°, the inner diameter of the cartridge is from 1.5 to 5 mm, preferably about 2.5 mm; the ratio between the length and the inner diameter of the cartridge is at least 10:1; and the outlet opening of the dispensing nozzle has an inner diameter of 1.5 to 3 mm, preferably about 2 mm. A container with these dimensions in specifically suited for applying a dental substance directly into a tooth cavity.

For storing light-sensitive substances, the cartridge and dispensing nozzle are preferably made of a material that is impermeable to radiation in the respective spectral range.

In another preferred embodiment, the cartridge and/or the dispensing nozzle have a specific colour for identifying the container contents. As compared to using a colour-coded closure cap, this feature has the advantage of avoiding any danger of confusion.

In another advantageous embodiment of the invention, the container is provided with a cap for closing the dispensing nozzle, thereby protecting the contents of the container during storage and shipping, the cap being provided with venting apertures for pressure compensation in case of external temperature or pressure changes.

BRIEF DESCRIPTION OF THE DRAWINGS

FIG. 1 is a longitudinal section through a container for a dental substance, shown in a disassembled state, with a closure cap.

FIG. 2 is a similar longitudinal section through a container according to a second embodiment.

FIG. 3 is an end view showing the rear end of the cartridge.

FIG. 4 is a cross-section through a closure cap that may be used with the container of FIG. 1 or that of FIG. 2.

DETAILED DESCRIPTION OF PREFERRED EMBODIMENTS

The container shown in FIG. 1 consists of a cartridge 10 and a separately manufactured dispensing nozzle 11. The cartridge 10 is constituted by a circular-cylindrical tube defining an axis 14 and having at its rear end an outwardly extending flange 12 for engagement by an applicator or dispensing instrument (not shown). The front end of the cartridge 10 is provided with an inner annular groove 13.

The dispensing nozzle 11 is formed by a tube which has a circular cross-section and is bent at a constant radius, the inlet end of the nozzle 11 having an enlarged portion 16 for engaging the annular groove 13 in the cartridge 10. At the inlet end, the centre line 17 of the nozzle 11 is aligned with the axis 14 of the cartridge 10; at the outlet end, however, the centre line 17 extends at an angle with respect to the axis 14 of at least 45° to 90°, preferably about 60°.

It is preferred for the dispensing nozzle 11 to be curved through a large angle. Shortening the nozzle 11 will then achieve the angle of the outlet opening which may be best suited for the respective purpose.

At the inlet end, the inner diameter of the dispensing nozzle 11 is the same as that of the cartridge 10. In the embodiment shown in FIG. 1, this inner diameter is 1.5 to 5 mm, preferably about 2.5 mm. The inner diameter of the nozzle 11 tapers toward the outlet end to a value of 1.5 to 3 mm, preferably about 2 mm, with the exact circular shape of the inner cross-section being maintained throughout the length of the nozzle 11. This shape ensures a laminar flow of the container contents and avoids changes in the material structure and properties of the substance.

The wall thickness of the curved dispensing nozzle 11 continuously decreases from the location of the annular groove 15 to the oulet end. This ensures high structural stability in combination with a fine tape that permits exact application of the container contents to small areas, such as dental cavities.

The annular groove 13 formed in the front end of the cartridge 10 and the enlarged portion 16 provided at the inlet end of the dispensing nozzle 11 are shaped complimentarily to form a snap-connection, in which the nozzle 11 is rotatable about the axis 14 relative to the cartridge 10. In dispensing the container contents, the oulet end of the nozzle 11 may thus be directed to the location of treatment under the most convenient angle, while the cartridge 10 is held stationary.

The container shown in FIG. 2 differs from that of FIG. 1 in that the dispensing nozzle 21 has a rear annular extension 28 of somewhat enlarged inner diameter which is fixedly embedded in the material of an enlarged flange 29 provided at the oulet end of the cartridge 20. The embedding is done in the course of a two-component injection moulding wherein the nozzle 21 is formed in a first step and the cartridge 20 is moulded in a second step in such a way that the extension 28 of the nozzle 21 is fused into the flange 29 of the cartridge 20.

The flange 12 provided at the rear end of the cartridge 10, 20 may have a circular-cylindrical outer surface. As shown in FIG. 3, however, it preferably has a shape different from a circular cylinder, specifically that of a hexagonal prism. This is advantageous for the handling of the container as the dispensing end of the nozzle 11 will retain its orientation with respect to the respective applicator engaging the cartridge 10, 20. The structure shown in FIG. 3 may be used with the cartridge of FIG. 1 just as with that of FIG. 2.

The cartridge 10, 20 and the nozzle 11, 21 are injection-moulded from synthetic resin. For storing a light-sensitive substance, the resin of both parts is impermeable to light. Preferably, the cartridge 10, 20 is black, whereas the dispensing nozzle 11, 21 has a specific colour to identify the container contents.

FIG. 1 shows a closure cap 30 with venting slots 31 close to its tip for pressure compensation, thereby to prevent pressure or temperature changes from exerting local forces on the part of the substance positioned at the outlet end of the nozzle 11. The same cap 30 may be provided for the container according to the embodiment of FIG. 2. Alternatively, rather than providing the venting slots 31 shown in FIG. 1, venting slots 32 may be provided in the form of axial grooves disposed in the inner wall of the cap 30 as illustrated in FIG. 4.

The container is distributed in the assembled condition, filled with the respective dental or other pasty substance, with the dispensing end of the nozzle 11, 21 being closed by the cap 30 and the flanged rear end being closed by a piston (not shown). For dispensing the contents, the container is inserted into an applicator which engages the cartridge 10, 20 at the flange 12 and which has a plunger for advancing the piston.

I claim:

1. A container for storing and dispensing a pasty substance sensitive to local pressure differences, comprising a cartridge for holding said substance, said cartridge being circular-cylindrical throughout its length and defining an axis, and a dispensing nozzle constituted by a rigid tube having an inlet opening which communicates with said cartridge, said inlet opening being the same size as the cartridge and aligned with said axis, and an outlet opening which is inclined with respect to said axis, the tube being circularly curved along a continuous smooth path throughout is length, and tapering toward said outlet opening in such a way that its inner cross-sectional shape is circular throughout its length.

2. The container of claim 1, wherein said dispensing nozzle is rotatable about said axis at the location of said inlet opening.

3. The container of claim 1, wherein said dispensing nozzle is retained by a snap-connection within an outlet end of said cartridge.

4. The container of claim 1, wherein said cartridge is moulded to said dispensing nozzle.

5. The container of claim 4, wherein said dispensing nozzle has a rear extension embedded in the material of said cartridge.

6. The container of claim 4, wherein said cartridge has a rear portion for engagement by a dispensing instrument, said rear portion having an external shape different from a circular cylinder.

7. The container of claim 1, wherein said dispensing nozzle has a wall thickness which decreases continually from said inlet opening to said oulet opening.

8. The container of claim 1, wherein outlet opening the of said dispensing nozzle defines an axis which extends at an angle of at least 45° to 90° with respect to the axis of said cartridge.

9. The container of claim 8, wherein axis defined by the outlet opening the of said dispensing nozzle extends at an angle of at least 60° with respect to the axis of sad cartridge.

10. The container of claim, wherein said cartridge has an inner diameter of 1.5 to 5 mm.

11. The container of claim 10, wherein the inner diameter of said cartridge is substantially 2.5 mm.

12. The container of claim 1, wherein the ratio of the length to the inner diameter of said cartridge is at least 10:1.

13. The container of claim 1, wherein the outlet opening of said dispensing nozzle has an inner diameter of 1.5 to 3 mm.

14. The container of claim 13, wherein the oulet opening of said dispensing nozzle has an inner diameter of substantially 2 mm.

15. The container of claim 1, wherein said cartridge and said dispensing nozzle are made of a material which is impermeable to light of a specific spectral range.

16. The container of claim 15, wherein one of said cartridge and dispensing nozzle has a colour identifying the container content.

17. The container of claim 1, further including a cap for closing said dispensing nozzle, the cap being provided with venting apertures.

* * * * *